United States Patent [19] [11] 4,172,855
Shubkin et al. [45] Oct. 30, 1979

[54] LUBRICANT

[75] Inventors: Ronald L. Shubkin, West Bloomfield; Ellis B. Rifkin, Southfield; Martin E. Gluckstein, Detroit, all of Mich.

[73] Assignee: Ethyl Corporation, Richmond, Va.

[21] Appl. No.: 894,722

[22] Filed: Apr. 10, 1978

[51] Int. Cl.$^2$ .............................. C07C 9/14; C07C 3/10
[52] U.S. Cl. .......................................... 585/16; 585/18; 585/255; 585/510; 585/511; 585/517; 585/532
[58] Field of Search .................. 260/676 R, 683.15 B, 260/683.15 D, 683.9

[56] References Cited

U.S. PATENT DOCUMENTS

| | | | |
|---|---|---|---|
| 3,330,883 | 7/1967 | Giannetti et al. | 260/683.15 B |
| 3,780,128 | 12/1973 | Shubkin | 260/683.15 B |
| 3,907,924 | 9/1975 | Isa et al. | 260/683.9 |
| 3,957,664 | 5/1976 | Heilman et al. | 260/683.15 B |
| 3,997,621 | 12/1976 | Brennan et al. | 260/683.15 B |
| 4,045,508 | 8/1977 | Cupples et al. | 260/683.15 B |

Primary Examiner—C. Davis
Attorney, Agent, or Firm—Donald L. Johnson; Robert A. Linn; Joseph D. Odenweller

[57] ABSTRACT

A process for making a low viscosity, low volatility α-olefin oligomer suitable for use as a functional fluid or lubricating oil comprising dimerizing a $C_{6\text{-}12}$ α-olefin, reacting the resultant dimer with a $C_{6\text{-}18}$ α-olefin in the presence of a Friedel-Crafts catalyst, distilling out volatile components and hydrogenating the residual product.

26 Claims, No Drawings

LUBRICANT

BACKGROUND OF THE INVENTION

α-Olefin oligomers have been used as functional fluids and lubricating oils. Many methods for making these oligomers are known. In U.S. Pat. No. 2,937,129 a $C_{5-14}$ α-olefin is oligomerized using a dialkyl peroxide catalyst. U.S. Pat. No. 3,149,178 describes a process of oligomerizing a $C_{6-12}$ α-olefin using a peroxide catalyst, Friedel-Crafts catalyst or heat followed by removal of dimer and hydrogenation of the residual product. U.S. Pat. No. 3,179,711 describes a process using as the catalyst the reaction product of $TiCl_4$, alkyl aluminum sesquihalide and tetraalkyl silicate. U.S. Pat. No. 3,330,883 describes a process for making an α-olefin oligomer without using expensive 1-dodecene by oligomerizing a mixture of at least one $C_{6-10}$ α-olefin and at least one $C_{14-16}$ α-olefin using a Friedel-Crafts catalyst. U.S. Pat. No. 3,382,291 describes an oligomer process in which a stream of boron trifluoride promoter complex are concurrently added to a reaction zone. In U.S. Pat. No. 3,576,898 a $C_{24-60}$ oligomer is made by dimerizing an α-olefin using a Ziegler catalyst followed by dimerization or trimerization of the dimer using a Friedel-Crafts catalyst.

The following patents are but a few of the many other methods described for making oligomers: U.S. Pat. Nos. 3,682,823; 3,763,244; 3,769,363; 3,780,128; 3,798,284; 3,884,988; 3,097,924; 3,997,621; 4,045,507 and 4,045,508.

In many uses it is preferred that the oligomer have a low viscosity, for example, below about 5 cs, and most preferably about 4 cs, at 210° F. These low viscosity oligomers are especially useful as engine lubricating oil in that they minimize friction and thus improve fuel economy. Used either alone or as blends with mineral oil they can provide lubricating oils with viscosities which qualify as SAE 5W 30 crankcase oils.

In attempting to make such low viscosity oligomers, an ever present problem is the volatility of the oligomer. As the oligomers are made less viscous their volatility increases such that a portion of the oligomer will vaporize at engine crankcase temperature. This results in apparent oil consumption and if excessive, can result in failing to pass the required ASTM IIId engine test.

If the volatile components are distilled out prior to blending the oil in order to avoid excessive vaporization, the viscosity of the oligomer increases sharply making them unsuitable for blending low viscosity oils. Thus, the oligomer producer finds himself on the horns of a dilemma.

In the past, useful oligomers having the desired viscosity and volatility properties have been made by oligomerizing 1-decene using a Friedel-Crafts catalyst followed by distillation of dimer and hydrogenation of the residue. However, 1-decene is in limited supply because it is a coproduct made together with a broad range of α-olefins. In order to provide more flexibility in making synthetic lubricating oil there exists a need for a process capable of using a broad range of α-olefins to produce an oligomer which will have the desired low viscosity, low volatility physical properties needed for a premium lubricating oil. The present invention provides such a process.

SUMMARY OF THE INVENTION

According to the present invention α-olefin oligomers having both low viscosity and low volatility are made by dimerizing a first α-olefin or mixture thereof and then reacting the dimer with a second α-olefin or mixture thereof in the presence of a Friedel-Crafts catalyst. The first and second α-olefins are selected such that double the average carbon number of the first α-olefin or mixture thereof plus the average carbon number of the second α-olefin or mixture thereof totals about 26-36. Components containing less than about 26 carbon atoms are distilled from the product leaving a residual product which is hydrogenated.

DESCRIPTION OF THE PREFERRED EMBODIMENT

A preferred embodiment of the invention is a process for making an α-olefin oligomer from at least two different alpha olefins, said process comprising contacting a first α-olefin containing about 6-12 carbon atoms or mixture thereof with an olefin dimerization catalyst to obtain an initial product consisting mainly of dimers of said first α-olefin, and then reacting said initial product with a second α-olefin containing about 6-18 carbon atoms or mixture thereof in the presence of a Friedel-Crafts catalyst to form an oligomer consisting mainly of a graft of said second α-olefin to said dimers, said first and said second α-olefins being selected such that two times the average carbon number of said first α-olefin or mixture thereof plus the average carbon number of said second α-olefin or mixture thereof is about 26-36, removing said Friedel-Crafts catalyst, distilling out oligomer containing up to about 26 carbon atoms and hydrogenating the remaining oligomer to obtain a hydrogenated olefin oligomer.

Examples of α-olefins containing 6-12 carbon atoms are 1-hexene, 1-heptene, 1-octene, 1-nonene, 1-decene, 1-undecene and 1-dodecene. Of these the more preferred are those of even carbon number, that is, 1-hexene, 1-octene, 1-decene and 1-dodecene.

Examples of α-olefins containing 6-18 carbon atoms are as above plus 1-tridecene, 1-tetradecene, 1-pentadecene, 1-hexadecene, 1-heptadecene and 1-octadecene. Of these the more preferred are those having an even carbon number.

The first and second olefins are selected such that twice the average carbon number of the first α-olefin or mixture thereof plus the average carbon number of the second α-olefin or mixture thereof is at least 26, preferably 26-36, and more preferably 28-34.

The average carbon number of an individual α-olefin is the number of carbon atoms per molecule, for example, 1-hexene is 6, 1-octene is 8, 1-decene is 10, etc. In olefin mixtures the average carbon number is the sum of the products obtained by multiplying the mole fraction of each olefin component times the number of carbon atoms in each such component. For example, the average carbon number for a 25-25-50 mole % mixture of 1-hexene, 1-octene and 1-dodecene, respectively, is $(0.25 \times 6) + (0.25 \times 8) + (0.50 \times 12) = 9.5$. Likewise, the average carbon number for a mixture of 10 mole % 1-dodecene plus 90 mole % 1-tetradecene is $(0.10 \times 12) + (0.90 \times 14) = 13.8$.

When using mixtures of α-olefins to obtain either the first or second α-olefin having a particular carbon number, it is preferred that the spread of actual molecular weight of the components in each mixture be fairly narrow, preferably not over 4 carbon number between the lowest and highest molecular weight α-olefin in the mixture. Thus, preferred mixtures are (1-hexene+1- octene+1-decene) or (1-hexene+1-octene) or (1-octene+1-decene+1-dodecene) or (1-hexene+1-decene) or (1-dodecene+1-tetradecene+1-hexadecene) or (1-octene+1-decene).

Following the process, if the first α-olefin has an average carbon number of 8, the second α-olefin will have an average carbon number of at least 10 (e.g. 10–20) and more preferably 12–16. Likewise, if the first α-olefin has an average carbon number of 10, the second α-olefin will have an average carbon number of 6–16, more preferably 8–14. This range does provide for the first and second α-olefins to have the same average carbon number. This is within the purview of the invention. However, this would not be the more preferred embodiment of the invention. In a more preferred embodiment of the invention the first α-olefin contains 6–10 carbon atoms and the second α-olefin contains 10–18 carbon atoms and each is selected such that twice the average carbon number of the first α-olefin or mixture thereof plus the average carbon number of the second α-olefin or mixture thereof is about 26–36, more preferably 28–34.

In a still more preferred embodiment, the first α-olefin is selected from 1-hexene and 1-octene and mixtures thereof and the second α-olefin is selected from 1-dodecene, 1-tetradecene, 1-hexadecene and 1-octadecene or mixtures thereof.

In a most preferred embodiment the first α-olefin is 1-octene and the second α-olefin is 1-tetradecene.

In any of the above-described embodiments minor amounts of other olefins which are not α-olefins or are outside the preferred molecular weight range can be used to the extent that they do not adversely affect the physical properties of the final product such that it is unsatisfactory for use as crankcase lubricating oil.

In the initial stage, the first α-olefin or mixture thereof is dimerized using one of the catalyst systems known to favor dimerization of α-olefins. Many such catalysts are known. A few examples are: triarylphosphine-nickel carbonyl complex, nickel salts of organic acid (e.g. nickel di-isopropylsalicylate), nickel complexes as described in U.S. Pat. No. 3,231,546, incorporated herein by reference, organo nickel sulfoxides plus alkyl aluminum halide as described in U.S. Pat. No. 3,327,015, incorporated herein by reference, nickel di-isopropyl salicylate plus dialkyl aluminum fluoride as described in U.S. Pat. No. 3,355,510, incorporated herein by reference, triphenylphosphine nitrosyl iodonickel or trimethyl arsine nitrosyl iodonickel plus a trialkyl aluminum or alkyl aluminum halide as described in U.S. Pat. No. 3,427,365, incorporated herein by reference, nickel acetyl acetonate plus an alkyl aluminum as described in U.S. Pat. No. 3,505,425, incorporated herein by reference, nickel halide-phosphine complex plus alkyl aluminum halide as described in U.S. Pat. No. 3,467,726, incorporated herein by reference, trialkyl aluminum as described in U.S. Pat. No. 3,576,898, incorporated herein by reference, ethyl aluminum dichloride plus [1,2-bis(diphenylphosphino)ethylene]dichloro nickel as described in U.S. Pat. No. 3,636,128, incorporated herein by reference and $BF_3$ plus $H_3PO_4$ plus $H_2O$ as described in U.S. Pat. No. 3,742,082, incorporated herein by reference.

The preferred dimerization catalysts are alkyl aluminum compounds such as trialkyl aluminum, dialkyl aluminum halide, alkyl aluminum dihalide, or alkyl aluminum sesquihalide. Alkyl groups can contain from 1–20 carbon atoms. Examples of such compounds are trimethyl aluminum, triethyl aluminum, tri-isopropyl aluminum, tri-isobutyl aluminum, tri-n-butyl aluminum, tri-isopentyl aluminum, tri-hexyl aluminum, tri-octyl aluminum, tri-eicosyl aluminum, methyl aluminum dichloride, ethyl aluminum dichloride, n-butyl aluminum dibromide, diethyl aluminum chloride, di-n-propyl aluminum bromide, di-n-butyl aluminum chloride, di-isobutyl aluminum chloride, di-n-dodecyl aluminum chloride, methyl aluminum sesquichloride, ethyl aluminum sesquichloride, n-propyl aluminum sesquichloride and the like.

More preferred dimerization catalysts are the trialkyl aluminums. Preferably the alkyl groups containing from 1 to about 20 carbon atoms. Representative examples of these are triethyl aluminum, tri-n-propyl aluminum, tri-isobutyl aluminum, tri-n-butyl aluminum, tri-n-hexyl aluminum, tri-n-octyl aluminum, tri-eicosyl aluminum and the like.

The amount of dimerization catalyst should be an amount which will promote the formation of dimers under the reaction conditions. A useful range is about 0.1–10 wt %, based on the weight of the first α-olefin.

The dimerization should be conducted at a temperature which maximizes the formation of dimer within a reasonable time. This can be carried out over a wide temperature range of about 50°–250° C. or higher depending upon the particular catalyst selected. A preferred temperature range is 100°–150° C.

The dimerization is preferably carried out under an inert atmosphere although this is not necessary. Good results have been achieved conducting the dimerization under a nitrogen atmosphere.

In general, the reaction is conducted under sufficient pressure to maintain the α-olefin in a liquid state at the reaction temperature. This can usually be achieved at atmospheric pressure. If desired, the reaction can be conducted under super-atmospheric pressure, for example, up to about 500 psig.

Following dimerization, the catalyst is deactivated. This can be accomplished by washing with water, aqueous acid, alcohol or aqueous alcohol. Good results have been achieved by washing with dilute aqueous sulfuric acid.

At this stage it is preferred that the initial product be distilled to remove unreacted first α-olefin which can be recycled. Alternatively, the unreacted first α-olefin can be left in the initial product and carried through the second stage. In the second stage, some of the first α-olefin will be grafted to dimers in the initial product and some will be polymerized to dimers, trimers and higher oligomers. These will be distilled out following the second stage if they are of too low a molecular weight. If they are high enough in molecular weight they will remain in the product to form a minor part of the final hydrogenated oligomer.

However, it is highly preferred that the initial product be distilled following the dimerization reaction to remove unreacted α-olefin monomer for recycle. The residual product can be used without further treatment in the second stage as long as it does not contain an excessive amount of trimer. Presence of some trimer up to about 25 wt % can be tolerated. If this first α-olefin contains 6–8 carbon atoms such trimers will contain 18–24 carbon atoms and will be removed in the final distillation. For example, if the first α-olefin is 1-hexene, the trimer will contain only 18 carbon atoms and if left in can be easily removed following the second stage reaction. If the first α-olefin is 1-octene, the trimer will contain 24 carbon atoms and can be removed following the second stage to obtain the proper product volatility.

Alternatively, the dimer can be isolated in fairly pure form by distillation. Residual trimer and higher oligomers can be used for other purposes such as hydraulic fluid, transformer oil, base lubricant for making grease, alkylate for making alkyl benzenes and the like.

Following this, the initial dimer-containing product is reacted with the second α-olefin in contact with a Friedel-Crafts catalyst. Preferred catalysts are the Friedel-Crafts metal halide catalyst such as aluminum chloride, aluminum bromide, zinc chloride, stannic chloride, gallium chloride and the like. The most preferred Friedel-Crafts catalyst is boron trifluoride in combination with a promoter. Such promoters are well known and include water, alkanols (e.g. methanol, ethanol, isopropanol, isobutanol, 2-ethylhexanol, dodecanol and the like), fatty acids (e.g. formic, acetic, propionic, butyric, valeric, hexanoic, octanoic, lauric, oleic, stearic and the like), fatty acid alkyl esters (e.g. methyl acetate, ethyl propionate, ethyl valerate, glycol monobutyrate, trimethylol propane, tripelargonate, 2-ethylhexyl octanoate, methyl oleate and the like), dialkyl ethers (e.g. diethyl ether, di-n-butyl ether, ethyl butyl ether and the like), dioxane, glycol ethers (e.g. ethylene glycol monomethyl ether, diethylene glycol di-isobutyl ether, propylene glycol monoethyl ether and the like), aliphatic ketones (e.g. acetone, methylethyl ketone, methylisobutyl ketone and the like) and cycloaliphatic ketones (e.g. cyclohexanone). More preferred promoters are water and alkanols such as isopropanol, n-octanol, 2-ethylhexanol and n-dodecanol.

The amount of promoter should be an amount which causes reaction of the second α-olefin with the dimer. A useful range is about 0.05–3 wt % based on dimer and second α-olefin.

The reaction can be conducted by mixing the second α-olefin with the dimer, adding the Friedel-Crafts catalyst and stirring at reaction temperature. A useful temperature range is about 0°–150° C., more preferably 20°–60° C.

Alternatively, the Friedel-Crafts catalyst can be added to the dimer and the second α-olefin added to this mixture over an extended period of time. In a highly preferred embodiment using boron trifluoride catalyst, the promoter (e.g. water, alkanol, etc.) is added to the mixture of dimer and second α-olefin and boron trifluoride is injected into the stirred mixture in an amount sufficient to keep the system saturated with boron trifluoride. Excess boron trifluoride can be injected so that the excess bubbles through the reaction mixture. The excess can be easily recycled.

The amount of second α-olefin should be an amount sufficient to supply about one mole of α-olefin per mole of dimer in the initial product. A useful range is about 0.8–1.5 moles of second α-olefin per mole of dimer. More preferably, about 0.9–1.2 moles of second α-olefin is used per mole of dimer.

The second stage reaction is conducted until most of the dimer has reacted with the second α-olefin. This usually takes from about 0.5–8 hours.

Following the second stage, the Friedel-Crafts catalyst is removed. This can be done by washing with water or preferably aqueous ammonia. Following this the product is distilled to remove volatile components containing less than about 26 carbon atoms per molecule. More preferably, the distillation is continued to remove components less than about 28 carbon atoms.

The residual product is then hydrogenated by conventional methods. For example, it can be hydrogenated in an autoclave under hydrogen pressure using a nickel catalyst. Alternatively, it can be passed through a fixed bed catalyst (e.g. nickel on kieselguhr support) under hydrogen pressure.

The following example illustrates the manner according to which the present oligomers are made.

EXAMPLE 1

In a reaction vessel was placed 400 gms 1-octene and 38.5 ml tri-n-butyl aluminum under a nitrogen atmosphere. While stirring, the solution was heated to reflux (121° C.) and stirred over the weekend. Temperature rose gradually and was maintained at about 130° C. It was then quenched with 100 ml 10% aqueous sulfuric acid, washed with water and dried over magnesium sulfate. The intermediate product analyzed by VPC as follows:

Octene: 15.73 area %
Dodecene: 4.79 area %
Octene dimer: 76.51 area %
Eicosene: 0.39 area %
Tetracosene: 1.67 area %

Octene and dodecene were distilled out. The dodecene apparently came from displacement of 1-butene from tri-n-butyl aluminum followed by reaction of this 1-butene with 1-octene. This could be avoided by use of trioctyl aluminum.

In a second reaction vessel was placed 100 gms (0.446 moles) of the above residual octene dimer, 87.5 gms (0.446 moles) of 1-tetradecene and 0.47 gms of $BF_3 \cdot 2H_2O$. The mixture was stirred at 20°–30° C. while $BF_3$ was periodically bubbled through the liquid (12.6 gms $BF_3$ used). After two hours 10 minutes the reaction was quenched by adding 50 ml water. It was then washed with dilute aqueous ammonia followed by water. It was dried over magnesium sulfate and filtered. The product was distilled up to 240° C. liquid temperature, 140° C. overhead temperature at 1 mm Hg abs to remove components containing less than 28 carbon atoms. The residual product was 80.3 wt % of the distillation charge. The residual product analyzed by VPC:

$C_{24}$: 1.48 area %
$C_{28}$: 10.72 area %
$C_{30-32}$: 78.82 area %
$C_{42-48}$: 7.26 area %

At this stage the residual product had the following physical property:

Viscosity: 40° C. 15.75 cs
Viscosity: 100° C. 3.81 cs
Viscosity Index: 137
Pour point: −45° F.

The residual product was then hydrogenated at 250° C. using a Ni/kieselguhr catalyst under 750 psig, to give a saturated oligomer. Physical properties of the hydrogenated oligomer were as follows:

Viscosity: 40° C. 17.53 cs
Viscosity: 100° C. 4.03 cs
Viscosity Index: 131
Pour point: −45° F.

The hydrogenated oligomer was subjected to a volatility test in which a sample was heated in an oven at 204° C. under a nitrogen atmosphere for 2 hours. It exhibited 8.4 wt % weight loss. For comparison, a product made by water promoted $BF_3$ catalyzed oligomerization of 1-decene after dimer removal and hydrogenation had a viscosity at 100° C. of 3.98 cs and gave an 11.4 wt % weight loss in the volatility test. This decene oligomer blended in 110 SUS neutral oil (12.6 wt % oligomer) together with conventional additives passed the ASTM IIId engine test which measures lubricant volatility and stability under severe use conditions.

Other olefins can be substituted in the above example. For example, 1-dodecene could be dimerized in the first stage and the dimer reacted with 1-hexene in the second stage. Likewise, an equal mole mixture of 1-octene plus 1-decene could be dimerized in the first stage and the dimer then reacted with an equal mole mixture of 1-dodecene plus 1-tetradecene. Similarly, 1-hexene could be dimerized in the first stage and the dimer reacted with 1-octadecene in the second stage.

The oligomers made by the present process are ideally suited for use as synthetic lubricating oil in internal combustion engines. They can be used as the entire base lubricant or can be blended with other lubricating oils including mineral oil, synthetic ester oils (e.g. di-2-ethylhexyl adipate, trimethylolpropane tripelargonate, etc.), alkyl benzene oils (e.g. di-dodecylbenzene, di-tetradecylbenzene, etc.) and the like. The lubricating oils are formulated to contain conventional lubricating oil additives such as calcium petroleum sulfonates, overbased magnesium alkylbenzene sulfonate, zinc dialkyldithiophosphates, VI improvers (e.g ethylene-propylene copolymers, polyalkylmethacrylates, etc.), ashless dispersants (e.g. polyisobutylenesuccinimides of tetraethylene pentamine, polyisobutylenephenol-formaldehyde-tetraethylene pentamine Mannich condensation products, etc.), and antioxidants (e.g. 4,4'-methylenebis(2,6-di-tert-butylphenol), α-di-methyl amino-2,6-di-tert-butyl-p-cresol, etc.).

The following example illustrates the formulation of a blended engine crankcase lubricant.

EXAMPLE 2

In a vessel place 9,000 parts 150 SUS neutral mineral oil, 1,000 parts hydrogenated oligomer from Example 1, sufficient zinc isobutyl amyl dithiophosphate to provide 0.07 wt % zinc, calcium alkylbenzene sulfonate (300 TBN) to provide 0.15 wt % calcium, 90 parts of a 65 wt % active polyisobutyl succinimide of tetraethylene pentamine. Stir the mixture until homogenous to obtain a useful crankcase lubricating oil.

We claim:

1. A process for making an α-olefin oligomer in a two-stage reaction, said process comprising contacting a first α-olefin containing about 6–12 carbon atoms or mixture thereof with an alkyl aluminum olefin dimerization catalyst to obtain an initial product consisting mainly of dimers of said first α-olefin, and then reacting said initial product with a second α-olefin containing about 6–18 carbon atoms or mixture thereof in the presence of a Friedel-Crafts catalyst to form an oligomer consisting mainly of a graft of said second α-olefin to said dimers, said first and said second α-olefins being selected such that two times the average carbon number of said first α-olefin or mixture thereof plus the average carbon number of said second α-olefin or mixture thereof is about 26–36, removing said Friedel-Crafts catalyst, distilling out oligomer containing less than about 26 carbon atoms and hydrogenating the remaining oligomer to obtain a hydrogenated olefin oligomer.

2. A process of claim 1 wherein said first α-olefin contains about 6–10 carbon atoms and said second α-olefin contains about 10–18 carbon atoms.

3. A process of claim 2 wherein said Friedel-Crafts catalyst is boron trifluoride in combination with a promoter selected from the group consisting of water, alkanol, alkylene glycol, polyalkylene glycol, dialkyl ether, fatty acid, fatty acid alkyl ester, aliphatic ketone and cycloaliphatic ketone.

4. A process of claim 3 wherein said promoter is water.

5. A process of claim 3 wherein said promoter is a $C_{1-20}$ alkanol.

6. A process of claim 3 wherein said promoter is a $C_{1-20}$ alkyl ester of a $C_{1-20}$ fatty acid.

7. A process of claim 2 wherein said dimerization catalyst is a trihydrocarbyl aluminum.

8. A process of claim 7 wherein said trihydrocarbyl aluminum is a tri-$C_{1-20}$ alkyl aluminum.

9. A process of claim 8 wherein said Friedel-Crafts catalyst is boron trifluoride in combination with a promoter.

10. A process of claim 9 wherein said promoter is selected from the group consisting of water, alkanol, alkylene glycol, polyalkylene glycol, dialkyl ether, fatty acid, fatty acid alkyl ester, aliphatic ketone and cycloaliphatic ketone.

11. A process of claim 10 wherein said promoter is water.

12. A process of claim 10 wherein said promoter is a $C_{1-20}$ alkanol.

13. A process of claim 10 wherein said promoter is a $C_{1-20}$ alkyl ester of a $C_{1-20}$ fatty acid.

14. A process of claim 11, 12 or 13 wherein said first α-olefin is a $C_{6-8}$ α-olefin and said second α-olefin is a $C_{12-18}$ α-olefin.

15. A process of claim 11, 12 or 13 wherein said first α-olefin is 1-octene and said second α-olefin is 1-tetradecene.

16. A process of claim 11, 12 or 13 wherein said trialkyl aluminum is tri-n-butyl aluminum, said first α-olefin is 1-octene and said second α-olefin is 1-tetradecene.

17. An α-olefin oligomer having a low viscosity and low volatility made by the process comprising contacting a first α-olefin containing about 6–12 carbon atoms or mixture thereof with an olefin dimerization catalyst to obtain an initial product consisting mainly of dimers of said first α-olefin, removing any remaining first α-olefin from said initial product and then reacting said initial product with a second α-olefin containing about 6–18 carbon atoms or mixture thereof in the presence of a Friedel-Crafts catalyst to form an oligomer consisting mainly of a graft of said second α-olefin to said dimers, said first and said second α-olefins being selected such that twice the average carbon number of said first α-olefin or mixture thereof plus the average carbon number of said second α-olefin or mixture thereof is about 26–36, removing said Friedel-Crafts catalyst, distilling out oligomer containing less than about 26 carbon atoms and hydrogenating the remaining oligomer to obtain a hydrogenated olefin oligomer.

18. An oligomer of claim 17 wherein said first α-olefin contains about 6–10 carbon atoms and said second α-olefin contains about 10–18 carbon atoms.

19. An oligomer of claim 18 wherein said Friedel-Crafts catalyst is boron trifluoride in combination with a promoter selected from the group consisting of water, alkanol, alkylene glycol, polyalkylene glycol, dialkyl ether, fatty acid, fatty acid alkyl ester, aliphatic ketone and cycloaliphatic ketone.

20. An oligomer of claim 19 wherein said promoter is water.

21. An oligomer of claim 19 wherein said promoter is a $C_{1-20}$ alkanol.

22. An oligomer of claim 18 wherein said dimerization catalyst is a tri-$C_{1-20}$ alkyl aluminum.

23. An oligomer of claim 22 wherein said Friedel-Crafts catalyst is boron trifluoride in combination with a water promoter.

24. An oligomer of claim 22 wherein said Friedel-Crafts catalyst is boron trifluoride in combination with a $C_{1-20}$ alkanol promoter.

25. An oligomer of claim 23 or 24 wherein said first α-olefin is selected from the group consisting of 1-hexene and 1-octene and said second α-olefin is selected from the group consisting of 1-dodecene, 1-tetradecene, 1-hexadecene and 1-octadecene.

26. An oligomer of claim 23 or 24 wherein said first α-olefin is 1-octene and said second α-olefin is 1-tetradecene.

* * * * *